United States Patent [19]

Bahrmann et al.

[11] 4,337,363

[45] Jun. 29, 1982

[54] PROCESS FOR THE PREPARATION OF 3-(4-METHYL-3-CYCLOHEXEN-1-YL) BUTYRALDEHYDE

[75] Inventors: Helmut Bahrmann, Hünxe; Boy Cornils, Dinslaken; Carl D. Frohning; Jürgen Weber, both of Oberhausen, all of Fed. Rep. of Germany

[73] Assignee: Ruhrchemie Aktiengesellschaft, Oberhausen, Fed. Rep. of Germany

[21] Appl. No.: 69,659

[22] Filed: Aug. 24, 1979

[30] Foreign Application Priority Data

Aug. 28, 1978 [DE] Fed. Rep. of Germany ....... 2837480

[51] Int. Cl.$^3$ ............................................. C07C 45/50
[52] U.S. Cl. .................................................... 568/444
[58] Field of Search ......................... 260/598; 568/444

[56] References Cited

U.S. PATENT DOCUMENTS 3,801,646  4/1974  Booth .
3,933,919  1/1976  Wilkinson ..................... 260/598 X
4,122,121  10/1978  Gray et al. ......................... 260/598

OTHER PUBLICATIONS

Kogami (I), Yukagaku, vol. 22, No. 6 (1973), pp. 316–320.
Kogami et al., Chem. Abs., vol. 79 (1973), 92400n.

*Primary Examiner*—Bernard Helfin
*Attorney, Agent, or Firm*—Sprung, Horn, Kramer & Woods

[57] ABSTRACT

In a process for the preparation of 3-(4-methyl-3-cyclohexen-1-yl) butyraldehyde by hydroformylation of limonene in the presence of a catalyst containing a metal of Group VIII of the Periodic Table, the improvement wherein a rhodium carbonyl complex containing additionally a triphenyl and/or trialkyl phosphine as ligands is used as catalyst and the reaction is conducted at a pressure of 100 to 350 bars and at a temperature of 110° to 160° C., the triphenyl or trialkyl phosphines or mixture thereof being present in an amount of 10 to 50 moles per gram atom of rhodium in the reaction mixture.

9 Claims, No Drawings

PROCESS FOR THE PREPARATION OF 3-(4-METHYL-3-CYCLOHEXEN-1-YL) BUTYRALDEHYDE

BACKGROUND OF THE INVENTION

1. Field of the Invention

The present invention relates to a process for the preparation of 3-(4-methyl-3-cyclohexen-1-yl)butyraldehyde by reacting limonene with hydrogen and carbon monoxide in the presence of a complex rhodium compound as catalyst.

DISCUSSION OF PRIOR ART 3-(4-Methyl-3-cyclohexen-1-yl)butyraldehyde is used as an ingredient of perfume compositions. The starting material for preparing it is limonene which is reacted with carbon monoxide and hydrogen in the presence of cobalt carbonyl compounds which contain trialkyl or triaryl phosphines as ligands in addition to carbon monoxide or in the presence of rhodium carbonyl complexes. (See. C.A. Vol. 79 (1973) 92400 n).

The selectivity of this process is unsatisfactory because the aldehyde desired is formed in a yield of only 42 to 52% based on limonene charged. For this reason, the process is not suitable for use on a commercial scale. Therefore, there was the problem to develop a process which permits the conversion of limonene into 3-(4-methyl-3-cyclohexen-1-yl)butyraldehyde with high selectivity and high yield.

SUMMARY OF THE INVENTION

The foregoing is provided, in accordance with the invention which provides a process for the preparation of 3-(4-methyl-3-cyclohexen-1-yl)butyraldehyde by hydroformylation of limonene in the presence of a catalyst which contains a metal of Group VIII of the Periodic Table, using, as catalyst, a rhodium carbonyl complex which contains additionally a triphenyl or trialkyl phosphine, as ligands, the process operating under pressures of 100 to 350 bars and at a temperature of 110 to 160, said triphenyl or trialkyl phosphine or mixture thereof being present in the reaction mixture in an amount of 10 to 50 moles per gram atom of rhodium.

Due to the use of the selected reaction conditions, up to 98% of the starting material may be converted into the aldehyde desired.

The use of the catalysts according to the invention insures that hydroformylation of the limonene takes place selectively in such a manner that the formyl group migrates exclusively to the terminal carbon atom of the double bond which is present outside of the ring. The rhodium catalyst is effective already in low concentration. Usually 50 to 200 ppm of rhodium calculated as metal and based on olefin are used.

It is possible in principle to use also higher concentrations of rhodium. An increase in the reaction rate is achieved thereby. The high price of rhodium which decisively influences the economy of the process stands in the way of the use of large amounts of catalyst.

The use of a pressure of 100 to 350 bars has the additional result that the reaction takes place at a high rate. A temperature of 100° to 160° C., preferably 120° to 140° C., is employed. The reaction is performed from 60 minutes to 5 hours. Generally, there are 40 to 60 moles of hydrogen and 60 to 40 moles of carbon monoxide per mole of limonene. The mole ratio of $H_2$ to CO is generally 1:0.9 to 0.9:1.

It is also important for the process according to the invention that the alkyl phosphine or aryl phosphine is used in a great excess based on rhodium present. The use of 10 to 50 moles of phosphine per gram atom of rhodium insures that the rhodium complex contains always phosphine ligands throughout the reaction.

While it is possible in principle to carry out the reaction without a solvent, the presence of a solvent has been found to be favorable. Suitable solvents include especially aliphatic and aromatic hydrocarbons such as hexane, octane, benzene, toluene and xylene. Usually the solvent is used in the same amount by weight as the olefin, but it is also possible to use the solvent in excess, e.g., in a ratio by weight of 2:1. Addition of a solvent to the reaction mixture increases the selectivity of the reaction with respect to formation of 3-(4-methyl-3-cyclohexene-1-yl)butyraldehyde. A restriction of the use of solvents, may, however, result in turn from economic considerations.

The reaction may be carried out continuously or discontinuously. Olefin, solvent and catalyst are charged to a suitable reactor. After the reaction temperature has been reached, carbon monoxide and hydrogen are introduced, the gas stream being rated such that the selected pressure is established. The proportion of hydrogen in the carbon monoxide-hydrogen mixture is usually about 30 to 70% by volume. The catalyst may have been preformed when added to the reaction mixture.

Formation of the catalyst in situ from a rhodium salt, e.g., rhodium-2-ethyl hexanoate, the phosphine and carbon monoxide and hydrogen has been found to be particularly favorable. In this case, the solvent, rhodium salt and phosphine are charged first, carbon monoxide and hydrogen are added and, after the catalytically active complex has been formed, the olefin is introduced.

Upon completion of the reaction, the aldehyde formed is separated from the reaction product by distillation. The catalyst remains in the distillation residue and may be returned into the reaction together with the solvent. However, it is also possible to separate first the catalyst in known manner, e.g., by treating the reaction mixture with steam or hydrogen, and then process the reaction product.

Further purification of the 3-(4-methyl-3-cyclohexen-1-yl)butyraldehyde may be effected by subjecting it again to fractional distillation.

Alkyl phosphines useful in the process of the invention include $C_1$–$C_{18}$ alkyl phosphines including in particular tributyl-, trioctyl-, tridecyl- and trilaurylphosphine.

Aryl phosphines useful in the process of the invention include $C_6$–$C_{12}$ carbocyclic aryl phosphines which can be substituted on the aryl ring with methyl, carboxylic, sulfonic groups. Particularly contemplated aryl phosphines include triphenylphosphine, diphos, tritolylphosphine.

In order to more fully illustrate the nature of the invention and the manner of practicing the same, the following example is set forth:

EXAMPLE

In a 4.4 liter autoclave of stainless steel are reacted 1 liter (860 g. = 6 moles) of limonene and 1 liter (870 g. = 9.5 moles) of toluene in the presence of 86 mg. (= 0.8 mmoles) of rhodium in the form of rhodium-2- ethyl hexanoate and 19.7 g. (=75 mmoles) of triphenyl phosphine at 150° C. and 280 bars with a 1:1 CO/H$_2$ mixture. After about 3 hours when no more gas is absorbed, the contents of the autoclave are cooled to room temperature. The subsequent processing of the hydroformylation product by distillation in a column having 12 theoretical plates at 30 Torr gives, at an overhead temperature of 35° C., 875 grams of first runnings containing toluene and, at 126° C. and a bottoms temperature of about 150° C., 793 g. of 3-(4-methyl-3-cyclohexen-1-yl)butyraldehyde corresponding to a yield of 76%, based on limonene charged.

The unsaturated aldehyde has a purity of 99.4% determined by gas chromatography.

We claim:

1. In a process for the preparation of 3-(4-methyl-3-cyclohexen-1-yl)butyraldehyde by hydroformylation of limonene in the presence of a catalyst containing a metal of Group VIII of the Periodic Table, the improvement wherein a rhodium carbonyl complex containing additionally a triphenyl and/or trialkyl phosphine as ligands is used as catalyst and the reaction is conducted at a pressure of 100 to 350 bars and at a temperature of 110° to 160° C., the triphenyl or trialkyl phosphines or mixtures thereof being present in an amount of 10 to 50 moles per gram atom of rhodium in the reaction mixture.

2. A process according to claim 1, characterized in that the reaction is carried out in the presence of a solvent, especially an aliphatic or aromatic hydrocarbon.

3. A process according to claim 1 wherein the rhodium catalyst is present such that the amount of rhodium is 50 to 200 parts per million or rhodium, calculated as meta, based on the amount of olefin.

4. A process according to claim 3 wherein hydrogen is employed in an amount of 40 to 60 mols of hydrogen per mol of limonene and carbon monoxide is employed in an amount of 60 to 40 mols of carbon monoxide per mol of limonene.

5. A process according to claim 4 wherein the molar ratio of hydrogen to carbon monoxide is 1:009 to 0.9:1.

6. A process according to claim 4 wherein a triphenyl phosphine is included in the reaction mixture.

7. A process according to claim 4 wherein said trialkyl phosphine is a tri-C$_1$ to C$_{18}$ alkyl phosphine.

8. A process according to claim 4 wherein said triphenyl phosphine is an aryl phosphine containing a C$_6$ to C$_{12}$ carbocyclic aryl ring which can be substituted on the aryl ring with methyl, carbocyclic or at least one sulfonic acid group.

9. A process according to claim 1, wherein the rhodium catalyst is formed in situ by adding to the reaction mixture rhodium in the form of rhodium-2-ethyl hexanoate and said triphenyl or trialkyl phosphine.

* * * * *